United States Patent [19]

Walker

[11] Patent Number: 4,852,583

[45] Date of Patent: Aug. 1, 1989

[54] AIRWAY ADAPTER

[75] Inventor: Arthur H. Walker, Canyon Country, Calif.

[73] Assignee: SpaceLabs, Inc., Bothell, Wash.

[21] Appl. No.: 4,359

[22] Filed: Jan. 16, 1987

[51] Int. Cl.[4] .............................................. A61B 5/08
[52] U.S. Cl. ..................................... 128/716; 128/719
[58] Field of Search ......... 128/200.26, 207.14–207.17, 128/716, 719, 730, 204.22, 205.12

[56] References Cited

U.S. PATENT DOCUMENTS

| | | | |
|---|---|---|---|
| 3,667,475 | 6/1972 | Venturelli et al. | 128/207.14 |
| 3,874,377 | 4/1975 | Davidson | 128/207.15 |
| 4,297,871 | 11/1981 | Wright et al. | 128/719 X |
| 4,558,708 | 12/1985 | Labuda et al. | 128/207.14 |
| 4,558,709 | 12/1985 | Aida et al. | 128/719 |
| 4,679,573 | 7/1987 | Parnoff et al. | 128/719 X |

FOREIGN PATENT DOCUMENTS 1113484  5/1968  United Kingdom ........... 128/207.15

Primary Examiner—Nyle L. Howell
Assistant Examiner—Angela D. Sykes
Attorney, Agent, or Firm—Seed and Berry

[57] ABSTRACT

A tubular airway adapter having a hollow interior and a cylindrical wall for providing a sample gas air flow. The adapter includes an annular channel in the cylindrical wall and a plurality of radial channels extending from the annular channel to the interior. The annular channel is in fluid communication with ambient atmosphere through a port in the cylindrical wall. The wall of the adapter increases in thickness from on either side of the annular channel towards the annular channel to provide a double conically shaped interior and a wall region which protrudes into the interior at the location of the annular channel.

6 Claims, 2 Drawing Sheets

U.S. Patent   Aug. 1, 1989   Sheet 1 of 2   4,852,583
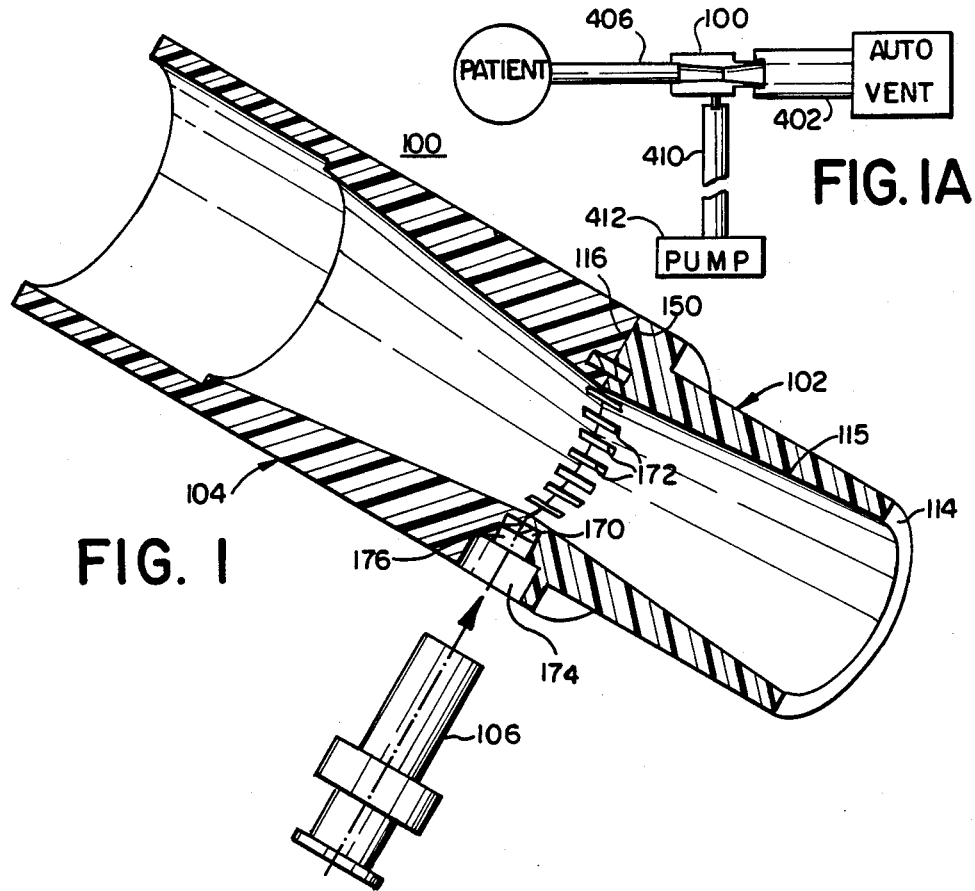
FIG. 1A
FIG. 1
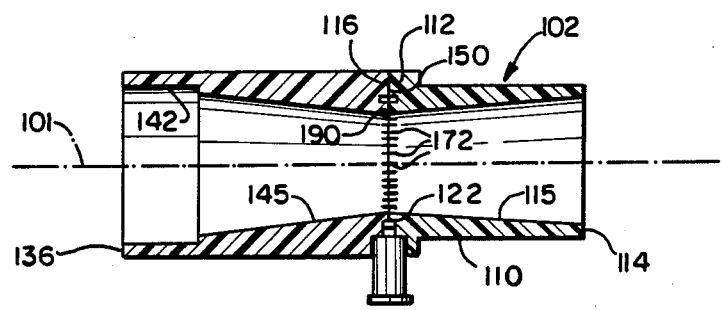
FIG. 2

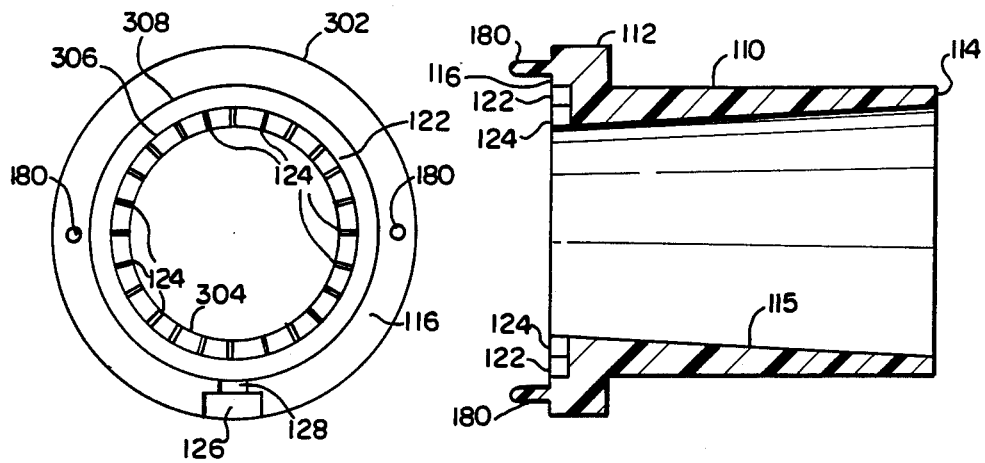
FIG. 3
FIG. 4
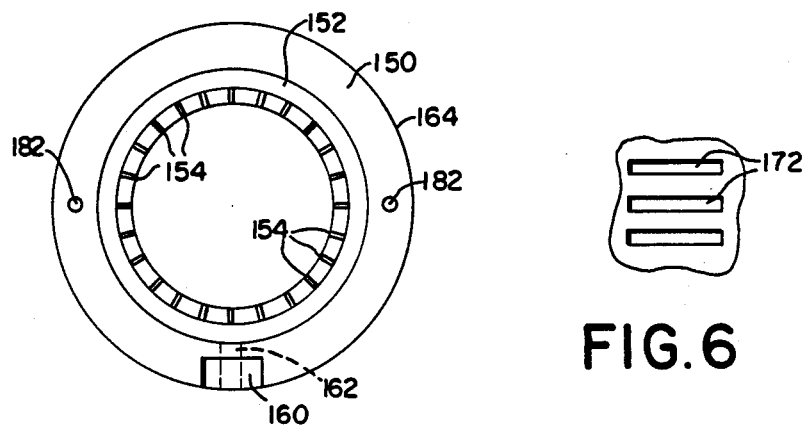
FIG. 5
FIG. 6

AIRWAY ADAPTER

BACKGROUND OF THE INVENTION

This invention relates to the field of medical gas sampling, more particularly for protecting medical gas sampling devices from contamination, obstruction and interfering substances.

Some patients receiving automatic ventilation through an artificial air tube are monitored for respiratory problems by drawing a small sample flow of gas from the air tube and continuously analyzing the level of carbon dioxide (capnography) or other gases. Typically, a sampling tube is connected to the air tube for conveying a sampled flow of gas from the air tube to the gas monitoring equipment, the diameter of the sampling tube being small compared to the diameter of the air tube.

Ventilated patients in the Intensive Care Unit (ICU) commonly have pulmonary problems with many secretions such as copious mucous sputum. These secretions are thixotropic gels which can and do solidify and adhere to a variety of surfaces, including the plastics used in medical tubing and related connectors and adapters used in gas monitoring devices.

In order to draw gas from the air tube, a vacuum is applied to one end of the sampling tube using, for example, a pump in the gas monitoring equipment. This can cause the above mentioned secretions to enter the gas sampling tube and gas monitoring equipment causing inaccurate measurement, or the entrance into the sampling tube can become blocked causing the sample gas flow to stop or become unacceptably low.

Some prior art devices use filtering materials over the sample port hole of airway adapters, but this slows down the sampling process relative to the respiration cycle of the patient.

SUMMARY OF THE INVENTION

It is an object of the present invention to provide an improved airway adapter for providing a sample gas flow and a method for making the same.

It is a further object of the present invention to prevent secretions and other solid and liquid contaminates from entering or blocking the sampling tube.

Another object of the present invention is to provide for quicker sampling of the gas stream relative to the respiration cycle of the patient.

Accordingly, an airway adapter for obtaining a sample gas flow is provided having a tubular body with a hollow interior and cylindrical walls. A plurality of radial channels provide fluid communication between the hollow interior and an annular channel in the cylindrical wall of the tubular body. The annular channel is in fluid communication with ambient atmosphere through a port located in the cylindrical wall.

In the preferred embodiment, the walls of the tubular body gradually increase from either side of the annular channel toward the annular channel. This creates an interior conical surface which narrows from on either side of the annular channel up to the region where the annular channel is located.

According to the present invention, a method of forming an airway adapter comprises forming two tubular members having cylindrical walls, a hollow interior and opposing faces for joining the two tubular members together. An annular groove is formed in each face along with a plurality of radial slots extending from the hollow interior to the annular groove. A cut out is formed in each face extending from the annular groove to the periphery of the cylindrical wall.

The two opposing faces are joined together in such a way that the annular grooves form an annular channel, the radial slots, a plurality of radial channels, and the cut out, a port in the wall of the adapter.

In the preferred embodiment, the cylindrical wall of each tubular member increases in thickness toward the opposing face.

BRIEF DESCRIPTION OF THE DRAWINGS

FIG. 1 is a greatly enlarged, cross sectional view of the present invention airway adapter taken along its longitudinal axis.

FIG. 1A is an overall block diagram schematic of an automated ventilation system using the adapter of FIG. 1.

FIG. 2 is an enlarged side view of the airway adapter of FIG. 1.

FIG. 3 is an end view of a first tubular portion of the airway adapter of FIG. 2.

FIG. 4 is a cross sectional view of the first tubular portion of the airway adapter of FIG. 3 taken along its longitudinal axis through the alignment pins shown in FIG. 3.

FIG. 5 is an end view of a second tubular portion of the airway adapter of FIG. 2.

FIG. 6 is a greatly enlarged view of a portion of the interior of the airway adapter of FIG. 2.

DETAILED DESCRIPTION OF THE DRAWINGS

FIG. 1 is a greatly enlarged, elevational, cross sectional view of a preferred embodiment airway tube adapter designated generally 100 taken along the longitudinal axis 101 in FIG. 2. The airway tube adapter 100 comprises three parts: a first tubular portion 102, a second tubular portion 104 and a sample tube connector 106.

Referring now to FIGS. 1 and 2, the first tubular portion 102 comprise a cylindrical body portion 110 having a first constant outer diameter along its entire length and integrally formed with a shoulder portion 112. The cylindrical wall of the first tubular portion tapers in thickness to create a conically shaped interior surface 115 with a larger diameter at its open end 114 opposite the shoulder portion 112 and a smaller diameter at the shoulder portion open end. The shoulder portion 112 presents an annular end surface 116 in a plane substantially perpendicular to the longitudinal axis 101 of the first tubular portion.

Referring now to FIGS. 1-4, the first tubular portion 102 further comprises an annular groove 122 in the annular end surface 116. The annular end surface 116 is perpendicular to the longitudinal axis 101. A plurality of equally spaced radially extending slots 124 are located in the annular end surface 116 which slots open up into the conical interior 115 and extend therefrom to the annular groove 122. As seen in FIG. 3, the annular end surface 116 further comprises a semi-cylindrical cut-out 126 and an adjoining coaxial, smaller diameter semi-cylindrical cut out 128 each having a common axis perpendicular to the longitudinal axis 101 of the airway tube adapter 100. Together the cut out 126 and 128 extend from the circumferential surface 302 of the shoulder 112 to the annular groove 122. FIG. 4 is an elevational cross section of the first tubular portion which cuts through diametrically opposite slots 124 taken along a diameter 90° from a diameter lying along the axis of the cut outs 126 and 128.

FIG. 3 is an end view of the first tubular portion 102 viewed from the shoulder end 112. In the preferred embodiment, the outside diameter of the shoulder is 0.750 inches (circle 302) while the internal diameter of the interior conical surface (circle 304) is 0.400 inches. FIG. 3 shows the slots 124 extending from the interior surface to the annular groove 122 which has a 0.472 inch diameter as measured by its centerline and a groove width of 0.032 inches. Circle 306 shows the smaller diameter of the groove of which circle 308 is the larger diameter. Cut out 126 has a diameter of 0.237 inches while cut out 128 has a 0.062 inch diameter.

Referring once again to FIGS. 1 and 2, the second tubular portion 104 is cylindrically shaped having a first constant outer diameter from one open end 136 to the opposite end. The interior surface has a constant diameter at surface 142 for a predetermined distance from end 136 whereupon it tapers in conical fashion 145 to a diameter at its opposite end which diameter equals or is substantially the same as the diameter of the interior conical surface of the first tubular portion 102 at the annular surface 116 formed by shoulder 112. The outer diameter of the second tubular portion 104 equals or is substantially the same as the outer diameter of the shoulder 112. As seen in FIG. 5, which is an end view of the second tubular portion 104 looking at the surface 150, the annular surface 150 of the second tubular portion 104 looks much like the annular surface 116 and includes an annular groove 152 of the same diameter and width as annular groove 122 in the end surface 116 of the first tubular portion. Annular surface 150 further includes a plurality equally spaced radially extending slots 154 which extend from and open up into the interior conical surface to the annular groove 152. There are, in the preferred embodiment, the same number of slots in the second tubular portion as in the first. Annular surface 150 comprises a first larger diameter cut out 160 adjoining a second, coaxial smaller diameter cut out 162 which together extend from the circumferential surface 164 of the second tubular portion to the annular groove 152.

When the surfaces 116 and 150 of the first and second tubular portions, respectively, are joined together and properly aligned the annular grooves come together to form an annular channel 170 in the airway adapter which is spaced apart from the hollow interior of the adapter and the slots come together to form a plurality of radial channels 172 allowing the interior of the hollow adapter to communicate with the annular channel 170. The semi-cylindrical cut outs, when aligned, form a first, larger diameter, cylindrical cavity 174 adjacent a second, smaller diameter, cylindrical cavity 176 which allows the annular channel 170 to be in fluid communication with the ambient atmosphere.

FIG. 6 is an enlarged detail of the radial channels 172 formed by the slots 124. Each channel is 0.002 inches high and 0.050 inches wide and there are, in the preferred embodiment, 36 of them equally spaced about at least a portion of the circumference.

In the preferred embodiment, the tubular portions 102 and 104 are made of a clear plastic and are joined together by gluing or sonic welding, for example. To provide for proper alignment when the two tubular portions are brought together, annular end surface 116 has two diametrically opposite pins 180 integrally formed with the first tubular portion 102 and extending perpendicularly away from surface 116. The pins are located between the annular groove 122 in the end surface and the outer periphery 302. Annular end surface 150 comprises two diametrically opposite holes 182 adapted to receive the pins 180 and in so doing align the opposing end surface 116 and 150. In the preferred embodiment the holes are 0.063 inches in diameter and 0.095 inches deep.

The sampling tube fitting 106 is also clear plastic and cylindrical in shape having a diameter just under the diameter of the cylindrical cavity 170. The diameters are such that when the fitting 106 is inserted into the cylindrical cavity 170 it forms a tight frictional fit. Glue or ultrasonic welding may also be used to provide a more secure bond between the fitting and the cavity.

In the preferred embodiment, the conical taper of the interior of the first tubular portion is 4° with a center line length of 0.753 inches, while the taper of the second tubular portion is 8° with a centerline length of 0.976 inches. When the two tubular portions 102 and 104 are brought together as just described the hollow interior of the adapter gradually narrows as gas flowing through the adapter passes from one end toward the junction of the two portions, and then the interior widens again as the gas flows towards the opposite end. At the junction region 190 the cross section of the interior is at its narrowest because the gradually thickening walls of the two tubular portions are thickest there. In the assembled adapter, the radial channels form slits through the junction region 190 where they open up into the interior. The slits are parallel with the longitudinal axis 101 of the adapter. The junction region may come to a peak, as in the preferred embodiment, but might also take on a convex shape if desired.

In operation, the cylindrical body portion 110 of the first tubular portion is adapted to fit within an airway tube 402 coupled to a respirator or automatic ventilator 404 while an endotracheal tube 406 coupled to the patient 408 fits within the cylindrical body of the second tubular portion at 142. A sampling air tube 410 is coupled to the connector 106 and is connected at its other end to a vacuum source 412.

The patient's exhalations or gas flow pass through the airway adapter generally along its longitudinal axis 101. The gas flow is channeled along the interior conical surface from the endotracheal tube picking up velocity as the adapter interior narrows. As the gas flow passes the junction region 190 through the slits formed therein by the radial channels 172, the gas has been compressed and expands into the radial channels 172. The slits insure good coupling between the radial channels and the gas flow.

Because of the vacuum created by pump 412 and the compression which takes place because of the narrowed region 190, the sampled gas flow is pulled through the radial channels 172, into and around the annular channel 170, and then through the cylindrical cavity 176, connector 106 and the sampling tube 410 connected to the connector 106. Because the radial channel cross sections are so small the likelihood that mucous or other solid or semi-solid matter will enter the sample tube is greatly reduced. Because there are a plurality of slots which surround the periphery of the adapter interior the likelihood that all sample gas flow will be stopped because of blockage is also greatly reduced. Because of the increased velocity mucous or other particulate matter is more likely to be pulled through the adapter 100 and less likely to enter the radial channels. The conical taper of the interior narrowing from the ends of the adapter to the radial channels causes a more rapid exhaustion of material from the slit area and this provides a more rapid response time relative to the patient's respiration cycle from the capnography equipment using the present invention adapter as compared with prior art adapters utilizing filter material over the sample port hole.

The adapter of the present invention provides good coupling to the gas flow, with minimal disturbance to the flow and reduced chance of significant blockage or contamination of the sample gas flow.

What is claimed is:

1. An airway adapter for obtaining a sample gas flow from a patient's exhalations, comprising:
    a tubular body having a cylindrical wall containing an annular channel, said cylindrical wall and annular channel surrounding a hollow interior for passing a gas flow therethrough, the thickness of at least a portion of the wall of said adapter gradually increasing along the direction of gas flow from one end of said tubular body to said annular channel to form a first conical interior surface, the thickness of at least a portion of the wall of said adapter gradually decreasing along the direction of gas flow from said annular channel to the other end of said tubular body to form a protruding region of said wall in said hollow interior in the region of said annular channel;
    a port in said wall providing fluid communication between said annular channel and ambient atmosphere; and
    a plurality of radial channels extending between the interior of said tubular body and said annular channel to provide fluid communication therebetween, said radial channels forming a plurality of parallel slits through said protruding region, said slits being substantially parallel to the longitudinal axis of said adapter.

2. An airway adapter for obtaining a sample gas flow from a patient's exhalations, comprising:
    a tubular body having a cylindrical wall containing an annular channel, said cylindrical wall and annular channel surrounding a hollow interior for passing a gas flow therethrough, the thickness of at least a portion of the wall of said adapter gradually increasing along the direction of gas flow from one end of said tubular body to said annular channel to form a first conical interior surface, the thickness of at least a portion of the wall of said adapter gradually decreasing along the direction of gas flow from said annular channel to the other end of said tubular body to form a protruding region of said wall in said hollow interior in the region of said annular channel;
    a port in said wall providing fluid communication between said annular channel and ambient atmosphere; and
    a plurality of radial channels extending between the interior of said tubular body and said annular channel to provide fluid communication therebetween, the height of each of said radial channel measured along the circumference of the interior of the adapter being substantially equal to or less than 0.002 inches.

3. The adapter of claim 2 wherein the length of each of said slits is substantially equal to or less than 0.050 inches.

4. A method of forming an adapter for obtaining a sample gas flow from a patient's exhalations, the sample gas flow being obtained by a sampling air tube, the method comprising the steps of:
    forming two annular members having cylindrical walls and a hollow interior and opposing faces adapted for mating engagement;
    forming an annular groove in each of said opposing faces;
    forming a plurality of radial slots in each of said opposing faces which extend from the hollow interior to said annular groove;
    forming a cut out in each of said faces which extends from said annular groove to the periphery of said cylindrical wall; and
    joining said opposing faces together in such a way that said annular grooves form an annular channel, said radial slots form a plurality of radial channels and said cut outs form a port providing fluid communications between said annular groove and said sampling air tube.

5. The method of claim 4 wherein said method further comprises forming a tapered cylindrical wall whose thickness increases toward said opposing face in each of said tubular members.

6. The method of claim 5 wherein said method further comprises the step of attaching a sampling tube connector to said joined tubular member in a cavity formed by said cut outs.

* * * * *

UNITED STATES PATENT AND TRADEMARK OFFICE
CERTIFICATE OF CORRECTION

PATENT NO. : 4,852,583

DATED : August 1, 1989

INVENTOR(S) : Arthur H. Walker

It is certified that error appears in the above-identified patent and that said Letters Patent is hereby corrected as shown below:

In claim 4, column 6, line 25, delete "annular" and substitute therefor --tubular--.

In claim 4, column 6, lines 39-40, delete "communications" and substitute therefor --communication--.

Signed and Sealed this

Twelfth Day of June, 1990

*Attest:*

HARRY F. MANBECK, JR.

*Attesting Officer*      *Commissioner of Patents and Trademarks*